(12) United States Patent
Dübal et al.

(10) Patent No.: US 6,495,220 B2
(45) Date of Patent: Dec. 17, 2002

(54) DISUBSTITUTED PHENANTHRENES AND THEIR USE IN LIQUID-CRYSTAL MIXTURES

(75) Inventors: Hans-Rolf Dübal, Eltville (DE); Barbara Hornung, Hasselroth (DE); Wolfgang Schmidt, Dreieich (DE); Rainer Wingen, Hattersheim (DE)

(73) Assignee: Clariant International Ltd., Muttenz (CH)

( * ) Notice: Subject to any disclaimer, the term of this patent is extended or adjusted under 35 U.S.C. 154(b) by 114 days.

(21) Appl. No.: 09/761,897

(22) Filed: Jan. 17, 2001

(65) Prior Publication Data

US 2001/0023935 A1 Sep. 27, 2001

(30) Foreign Application Priority Data

Jan. 19, 2000 (DE) .......................... 100 02 186

(51) Int. Cl.$^7$ .......................... C09K 19/32; C07C 23/44
(52) U.S. Cl. .................. 428/1.1; 252/299.62; 560/183; 560/187
(58) Field of Search ...................... 252/299.62; 428/1.1; 560/183, 187

(56) References Cited

U.S. PATENT DOCUMENTS

| | | | | |
|---|---|---|---|---|
| 5,648,021 A | * | 7/1997 | Wingen et al. | ........ 252/299.62 |
| 5,888,422 A | * | 3/1999 | Manero et al. | ........ 252/299.62 |
| 6,168,838 B1 | * | 1/2001 | Schmidt et al. | ............... 428/1.1 |
| 6,171,519 B1 | * | 1/2001 | Nonaka et al. | ........ 252/299.61 |

FOREIGN PATENT DOCUMENTS

| | | |
|---|---|---|
| DE | 195 00 768 A1 | 9/1995 |
| WO | WO 98/27035 | 6/1998 |
| WO | WO 98/27043 | 6/1998 |
| WO | WO 99/24385 | 5/1999 |

* cited by examiner

*Primary Examiner*—Shean C. Wu
(74) *Attorney, Agent, or Firm*—Frommer Lawrence & Haug

(57) ABSTRACT

Compounds of the formula (I)

$$R^1-A-Z^1 \qquad (I)$$

in which:

$R^1$ is an alkyl radical having 1 to 8 carbon atoms or an alkenyl radical having 2 to 8 carbon atoms, where, in each case, one (nonterminal) —$CH_2$— group may also be replaced by —O— or —C(=O)O— and/or one or more H may be replaced by F A is phenanthrene-2,7-diyl or 9,10-dihydrophenanthrene-2,7-diyl $Z^1$ is F, $OCH_xF_{3-x}$ or $CH_xF_{3-x}$, where, in each case, x is 0, 1 or 2, $OC_2H_zF_{5-z}$ or $C_2H_zF_{5-z}$, where, in each case, z is 0, 1, 2, 3 or 4, $CH=CF_2$ or Cl, with the proviso that 2-fluoro-7-methoxy-phenanthrene is excluded.

7 Claims, No Drawings

DISUBSTITUTED PHENANTHRENES AND THEIR USE IN LIQUID-CRYSTAL MIXTURES

Phenanthrene derivatives for use in liquid-crystalline mixtures have already been disclosed in DE-A 19500768, WO 98/27043, WO 98/27035 or WO 99/24385.

However, since the development of liquid-crystal mixtures can in no way be regarded as complete, display manufacturers are interested in a wide variety of components for mixtures.

In particular, liquid-crystal mixtures are required which have a very broad operating temperature range, but also a very low threshold voltage, for example for use in automobiles, in which a temperature range from −40 to 100° C. can easily occur, but also for portable devices such as mobile telephones and notebook PCs. Moreover, it appears that the tendency toward moving images can be realized with nematic liquid crystals only when the electrode separation of such LCDs is reduced, since the response times are inversely proportional to the square of the electrode separation. This in turn inevitably results in a reduction in brightness and contrast, unless liquid-crystal mixtures having a high optical anisotropy (delta n) value are used. However, materials having a high optical anisotropy usually have high viscosities as well and are thus unfavorable for the objective intended.

There is thus a need for novel, suitable liquid-crystal mixtures and mixture components for these which have a high clearing point and a high optical anisotropy and at the same time have a relatively low rotational viscosity.

It is therefore the object of the present invention to provide novel components for use in nematic or cholesteric liquid-crystal mixtures which have positive dielectric anisotropy values combined with a favorable viscosity/clearing point ratio. Moreover, the compounds should have a high light and UV stability and thermal stability. They should furthermore be suitable for realizing high voltage holding ratios (VHR). They should also be readily obtainable synthetically and thus potentially inexpensive.

It has now been found that these requirements are satisfied in a particular manner by compounds of the formula (I)

$$R^1\text{—A—}Z^1 \qquad (I)$$

in which:
  $R^1$ is an alkyl radical having 1 to 8 carbon atoms or an alkenyl radical having 2 to 8 carbon atoms, where, in each case, one (nonterminal) —$CH_2$— group may also be replaced by —O— or —C(=O)O— and/or one or more H may be replaced by F
  A is phenanthrene-2,7-diyl or 9,10-dihydrophenanthrene-2,7-diyl
  $Z^1$ is F, $OCH_xF_{3-x}$ or $CH_xF_{3-x}$, where, in each case, x is 0, 1 or 2, $OC_2H_zF_{5-z}$ or $C_2H_zF_{5-z}$, where, in each case, z is 0, 1, 2, 3 or 4, CH=$CF_2$ or Cl,
with the proviso that 2-fluoro-7-methoxy-phenanthrene is excluded.

Preference is given to those compounds of the formula (I) in which
  $R^1$ is an alkyl radical having 2 to 7 carbon atoms or an alkenyl radical having 2 to 7 carbon atoms, where, in each case, one (nonterminal) —$CH_2$— group may also be replaced by —O— and/or one or more H may be replaced by F
  A is phenanthrene-2,7-diyl or 9,10-dihydrophenanthrene-2,7-diyl
  $Z^1$ is F, $OCF_3$, $CF_3$, $OCHF_2$, $CHF_2$.

Particular preference is given to those compounds of the formula (I) in which
  $R^1$ is an alkyl radical having 2 to 7 carbon atoms or an alkenyl radical having 2 to 7 carbon atoms or an alkyloxy radical having 2 to 6 carbon atoms or an alkenyloxy radical having 2 to 6 carbon atoms
  A is phenanthrene-2,7-diyl or 9,10-dihydrophenanthrene-2,7-diyl
  $Z^1$ is F, $OCF_3$, $CF_3$.

Very particular preference is given to those compounds of the formula (I) in which
  $R^1$ is a linear alkyl radical having 2 to 7 carbon atoms or a linear alkyloxy radical having 2 to 6 carbon atoms
  A is phenanthrene-2,7-diyl
  $Z^1$ is F, $OCF_3$, $CF_3$.

Very particular preference is likewise given to those compounds of the formula (I) in which
  $R^1$ is a linear alkyl radical having 2 to 7 carbon atoms or a linear alkyloxy radical having 2 to 6 carbon atoms
  A is 9,10-dihydrophenanthrene-2,7-diyl
  $Z^1$ is F, $OCF_3$, $CF_3$.

Special preference is given to
2-ethyl-7-fluoro-phenanthrene
2-fluoro-7-propyl-phenanthrene
2-butyl-7-fluoro-phenanthrene
2-fluoro-7-pentyl-phenanthrene
2-fluoro-7-hexyl-phenanthrene.

Special preference is likewise given to
2-ethyl-7-fluoro-9,10-dihydrophenanthrene
2-fluoro-7-propyl-9,10-dihydrophenanthrene
2-butyl-7-luoro-9,10-dihydrophenanthrene
2-fluoro-7-pentyl-9,10-dihydrophenanthrene
2-fluoro-7-hexyl-9,10-dihydrophenanthrene.

The compounds of the formula (I) are used in liquid-crystal mixtures, preferably in nematic or cholesteric liquid-crystal mixtures. The liquid-crystal mixtures of the invention comprise at least one compound of the formula (I), preferably in an amount of 1 to 40% by weight, based on the liquid-crystal mixture. They preferably comprise at least 3 further components. The invention also provides a liquid-crystal display comprising these liquid-crystal mixtures.

The examples which follow illustrate the invention.

EXAMPLE 1

2-Fluoro-7-propyloxy-phenanthrene

A mixture of 20 mmol of 1-(3-fluorophenyl)-2-(2-bromo-5-propyloxyphenyl)-ethene [prepared by Wittig reaction of 3-fluorobenzyltriphenylphosphonium bromide and 2-bromo-5-propyloxybenzaldehyde in THF in the presence of potassium tert-butylate; 2-bromo-5-propyloxybenzaldehyde was prepared similarly to the method described by Astles, P. C., J. Med. Chem. 41, 2745 (1998)], 50 ml of diethyl ether and 10 mmol of cobalt(II) chloride (anhydrous) is refluxed, and an excess (as described in Gazz. Chim. Ital. 1966, 96,1792–1805) of a methylmagnesium iodide solution in ether is added dropwise over the course of about 1 h. After addition is complete, refluxing is continued for about 1 h. The mixture is cooled, hydrolyzed by adding about 100 ml of water and then acidified with hydrochloric acid. The organic phase is separated, washed with diluted sodium bicarbonate solution and water and dried using sodium sulfate. The solvent is removed under reduced pressure. Purification of the raw product [by column chromatography (silica gel, toluene) followed by recrystallization from acetonitrile] yields the product in the form of colorless crystals.

The following compounds can be obtained in a similar manner:
2-fluoro-7-methyl-phenanthrene
2-fluoro-7-ethyl-phenanthrene
2-fluoro-7-propyl-phenanthrene
2-fluoro-7-butyl-phenanthrene
2-fluoro-7-pentyl-phenanthrene
2-fluoro-7-hexyl-phenanthrene
2-fluoro-7-methoxy-phenanthrene
2-fluoro-7-ethoxy-phenanthrene
2-fluoro-7-butyloxy-phenanthrene
2-fluoro-7-pentyloxy-phenanthrene
2-fluoro-7-hexyloxy-phenanthrene.

EXAMPLE 2

2-Propyloxy-7-trifluoromethoxy-phenanthrene

Similarly to the method described by Kumar, S., J.Org.Chem. 62, 8535 (1997), 2-bromo-5-methoxy-benzaldehyde (for preparation see Ex. 1) and 4-trifluoromethoxyphenylboronic acid {prepared in a conventional manner from 4-trifluoromethoxy-bromobenzene [407-14-7]} are reacted to give 2-formyl-4-propyloxy-4'-trifluoromethoxy-biphenyl. Similarly to the method described in the same reference, this compound is reacted with trimethylsulfonium iodide under phase transfer conditions to give the corresponding oxiranyl derivative which can be isolated, but can alternatively advantageously be directly converted into the target compound by reaction with methanesulfonic acid (as described by Kumar, loc. cit.). Aqueous workup can be followed by purification as described in Ex. 1.

The following compounds can be obtained in a similar manner:
2-trifluoromethoxy-7-methyl-phenanthrene
2-trifluoromethoxy-7-ethyl-phenanthrene
2-trifluoromethoxy-7-propyl-phenanthrene
2-trifluoromethoxy-7-butyl-phenanthrene
2-trifluoromethoxy-7-pentyl-phenanthrene
2-trifluoromethoxy-7-hexyl-phenanthrene
2-trifluoromethoxy-7-methoxy-phenanthrene
2-trifluoromethoxy-7-ethoxy-phenanthrene
2-trifluoromethoxy-7-butyloxy-phenanthrene
2-trifluoromethoxy-7-pentyloxy-phenanthrene
2-trifluoromethoxy-7-hexyloxy-phenanthrene.

The following compounds can be obtained in a similar manner, but using 4-bromobenzotrifluoride [402-43-7]:
2-trifluoromethyl-7-methyl-phenanthrene
2-trifluoromethyl-7-ethyl-phenanthrene
2-trifluoromethyl-7-propyl-phenanthrene
2-trifluoromethyl-7-butyl-phenanthrene
2-trifluoromethyl-7-pentyl-phenanthrene
2-trifluoromethyl-7-hexyl-phenanthrene
2-trifluoromethyl-7-methoxy-phenanthrene
2-trifluoromethyl-7-ethoxy-phenanthrene
2-trifluoromethyl-7-propyloxy-phenanthrene
2-trifluoromethyl-7-butyloxy-phenanthrene
2-trifluoromethyl-7-pentyloxy-phenanthrene
2-trifluoromethyl-7-hexyloxy-phenanthrene.

EXAMPLE 3

2-Fluoro-7-propyloxy-9,10-dihydrophenanthrene

Is obtained by hydrogenating the compound of Ex. 1 in tetrahydrofuran at room temperature in the presence of 5% by weight of Pd (10% on activated carbon). Filtration is followed by purification as described in Ex. 1.

The following compounds can be obtained in a similar manner:
2-fluoro-7-methyl-9,10-dihydrophenanthrene
2-fluoro-7-ethyl-9,10-dihydrophenanthrene
2-fluoro-7-propyl-9,10-dihydrophenanthrene
2-fluoro-7-butyl-9,10-dihydrophenanthrene
2-fluoro-7-pentyl-9,10-dihydrophenanthrene
2-fluoro-7-hexyl-9,10-dihydrophenanthrene
2-fluoro-7-methoxy-9,10-dihydrophenanthrene
2-fluoro-7-ethoxy-9,10-dihydrophenanthrene
2-fluoro-7-butyloxy-9,10-dihydrophenanthrene
2-fluoro-7-pentyloxy-9,10-dihydrophenanthrene
2-fluoro-7-hexyloxy-9,10-dihydrophenanthrene
2-trifluoromethoxy-7-methyl-9,10-dihydrophenanthrene
2-trifluoromethoxy-7-ethyl-9,10-dihydrophenanthrene
2-trifluoromethoxy-7-propyl-9,10-dihydrophenanthrene
2-trifluoromethoxy-7-butyl-9,10-dihydrophenanthrene
2-trifluoromethoxy-7-pentyl-9,10-dihydrophenanthrene
2-trifluoromethoxy-7-hexyl-9,10-dihydrophenanthrene
2-trifluoromethoxy-7-methoxy-9,10-dihydrophenanthrene
2-trifluoromethoxy-7-ethoxy-9,10-dihydrophenanthrene
2-trifluoromethoxy-7-propyloxy-9,10-dihydrophenanthrene
2-trifluoromethoxy-7-butyloxy-9,10-dihydrophenanthrene
2-trifluoromethoxy-7-pentyloxy-9,10-dihydrophenanthrene
2-trifluoromethoxy-7-hexyloxy-9,10-dihydrophenanthrene
2-trifluoromethyl-7-methyl-9,10-dihydrophenanthrene
2-trifluoromethyl-7-ethyl-9,10-dihydrophenanthrene
2-trifluoromethyl-7-propyl-9,10-dihydrophenanthrene
2-trifluoromethyl-7-butyl-9,10-dihydrophenanthrene
2-trifluoromethyl-7-pentyl-9,10-dihydrophenanthrene
2-trifluoromethyl-7-hexyl-9,10-dihydrophenanthrene
2-trifluoromethyl-7-methoxy-9,10-dihydrophenanthrene
2-trifluoromethyl-7-ethoxy-9,10-dihydrophenanthrene
2-trifluoromethyl-7-propyloxy-9,10-dihydrophenanthrene
2-trifluoromethyl-7-butyloxy-9,10-dihydrophenanthrene
2-trifluoromethyl-7-pentyloxy-9,10-dihydrophenanthrene
2-trifluoromethyl-7-hexyloxy-9,10-dihydrophenanthrene.

EXAMPLE 4

A nematic test mixture MLC-9000-100 (from Merck KGaA, Darmstadt, Germany) is admixed with 5% of the compound of Ex. 1; the following improvements are obtained in comparison with the values of the mixture MLC-9000-100 given in parentheses:

clearing point=92° C. (90.5° C.) rotational viscosity=195 mPas (201 mpas) Delta n=0.12 (0.1137).

What claimed is:

1. A compound of the formula (I)

$$R^1—A—Z^1 \qquad (I)$$

in which:

$R^1$ is an alkyl radical having 1 to 8 carbon atoms or an alkenyl radical having 2 to 8 carbon atoms, where, in each case, one (nonterminal) —$CH_2$— group may also be replaced by —O— or —C(=O)O— and/or one or more H may be replaced by F A is phenanthrene-2,7-diyl or 9,10-dihydrophenanthrene-2,7-diyl $Z^1$ is F, $OCH_xF_{3-x}$ or $CH_xF_{3-x}$, where, in each case, x is 0, 1 or 2, $OC_2H_zF_{5-z}$ or $C_2H_zF_{5-z}$, where, in each case, z is 0, 1, 2, 3 or 4, CH=$CF_2$ or Cl, with the proviso that 2-fluoro-7-methoxy-phenanthrene is excluded.

2. A compound as claimed in claim 1, wherein, in the formula (I), $R^1$ is a linear alkyl radical having 2 to 7 carbon atoms or a linear alkyloxy radical having 2 to 6 carbon atoms and $Z^1$ is F, $CF_3$ or $OCF_3$.

3. A liquid-crystal mixture comprising at least one compound of the formula (I) as claimed in claim 1.

4. A liquid-crystal mixture as claimed in claim 3, which comprises the compound(s) of the formula (I) in an amount of 1 to 40% by weight, based on the liquid-crystal mixture.

5. A liquid-crystal mixture as claimed in claim 3, which is nematic or cholesteric.

6. A liquid-crystal mixture as claimed in claim 3, which comprises, in addition to the compounds of the formula (I), at least 3 further components.

7. A liquid-crystal display comprising a liquid-crystal mixture as claimed in claim 3.

* * * * *